United States Patent
Stenqvist et al.

(10) Patent No.: US 10,881,822 B2
(45) Date of Patent: Jan. 5, 2021

(54) METHOD, SYSTEM AND SOFTWARE FOR PROTECTIVE VENTILATION

(71) Applicant: The Lung Barometry Sweden AB, Viken (SE)

(72) Inventors: Ola Stenqvist, Viken (SE); Stefan Lundin, Gothenburg (SE)

(73) Assignee: THE LUNG BAROMETRY SWEDEN AB, Viken (SE)

( * ) Notice: Subject to any disclaimer, the term of this patent is extended or adjusted under 35 U.S.C. 154(b) by 239 days.

(21) Appl. No.: 15/574,468

(22) PCT Filed: May 25, 2016

(86) PCT No.: PCT/EP2016/061866
§ 371 (c)(1),
(2) Date: Nov. 15, 2017

(87) PCT Pub. No.: WO2016/189069
PCT Pub. Date: Dec. 1, 2016

(65) Prior Publication Data
US 2018/0140793 A1    May 24, 2018

(30) Foreign Application Priority Data

May 25, 2015 (SE) .................................... 1550671

(51) Int. Cl.
*A61M 16/00* (2006.01)
*A61B 5/08* (2006.01)
*A61B 5/091* (2006.01)

(52) U.S. Cl.
CPC ............ *A61M 16/024* (2017.08); *A61B 5/08* (2013.01); *A61B 5/091* (2013.01); *A61M 16/026* (2017.08);
(Continued)

(58) Field of Classification Search
CPC ........ A61B 5/08; A61B 5/091; A61M 16/024; A61M 16/026; A61M 2016/0027; A61M 2205/502; A61M 2230/40
See application file for complete search history.

(56) References Cited

U.S. PATENT DOCUMENTS

| 8,701,663 B2 * | 4/2014 | Stenqvist ................. A61B 5/08 128/204.21 |
| 2003/0111078 A1 * | 6/2003 | Habashi .............. A61M 16/024 128/204.18 |

(Continued)

FOREIGN PATENT DOCUMENTS

JP    S63 292965 A    11/1988

OTHER PUBLICATIONS

Bikker et al.,End-expiratory lung volume during mechanical ventilation: a comparison with reference values and the effect of positive end-expiratory pressure in intensive care unit patients with different lung conditions., Nov. 20, 2008, Critical Care, vol. 12 No. 6, Figure 1 and its description (Year: 2008).*

(Continued)

*Primary Examiner* — Samchuan C Yao
*Assistant Examiner* — Nathan M Le
(74) *Attorney, Agent, or Firm* — Knobbe, Martens, Olson & Bear, LLP

(57) ABSTRACT

A system including a breathing apparatus and a processor is configured to raise a first positive end-expiratory pressure PEEP level to at least a second PEEP level above said first PEEP level and subsequently lowering said second PEEP level to said first PEEP level and to calculate a lung mechanics equation relating total lung volume above functional residual capacity (FRC) to transpulmonary pressure (PTP) of a lung connected to said breathing apparatus, based (Continued)

on a change in end-expiratory lung volume (DEELV) between said first PEEP level and said second PEEP level.

17 Claims, 8 Drawing Sheets

(52) U.S. Cl.
CPC ............... *A61M 2016/0027* (2013.01); *A61M 2205/502* (2013.01); *A61M 2230/40* (2013.01)

(56) References Cited

U.S. PATENT DOCUMENTS

| | | | | |
|---|---|---|---|---|
| 2004/0249301 | A1* | 12/2004 | Stenqvist | A61B 5/0836 600/538 |
| 2006/0211950 | A1* | 9/2006 | Brunner | A61B 5/085 600/538 |
| 2007/0062532 | A1* | 3/2007 | Choncholas | A61M 16/0051 128/204.23 |
| 2007/0062533 | A1* | 3/2007 | Choncholas | A61B 5/091 128/204.23 |
| 2008/0295839 | A1* | 12/2008 | Habashi | A61M 16/0069 128/204.22 |
| 2009/0301492 | A1* | 12/2009 | Wysocki | A61B 5/085 128/204.23 |
| 2010/0228142 | A1* | 9/2010 | Sinderby | A61B 5/08 600/533 |
| 2011/0029910 | A1* | 2/2011 | Thiessen | A61M 16/0051 715/771 |
| 2012/0010520 | A1 | 1/2012 | Brochard et al. | |
| 2013/0174846 | A1* | 7/2013 | Stenqvist | A61B 5/08 128/204.23 |
| 2014/0288085 | A1* | 9/2014 | Yadav | A61K 31/519 514/250 |
| 2016/0000358 | A1* | 1/2016 | Lundin | A61B 5/08 600/532 |
| 2016/0038057 | A1* | 2/2016 | Johnson | A61B 5/087 600/533 |
| 2017/0273573 | A1* | 9/2017 | Tusman | A61B 5/091 |
| 2018/0339120 | A1* | 11/2018 | Vicario | A61B 5/0871 |
| 2019/0374733 | A1* | 12/2019 | Vicario | A61M 16/024 |

OTHER PUBLICATIONS

Grivans et al., Positive end-expiratory pressure-induced changes in end-expiratory lung volume measured by spirometry electric impedance tomography, 2011, Acta Anaesthesiologica Scandinavica, p. 1068-1077 (Year: 2011).*

International Preliminary Report on Patentability for PCT/EP2016/061866 (dated Nov. 28, 2017).

International Search Report and Written Opinion for International Application No. PCT/EP2016/061866 dated Aug. 1, 2016.

* cited by examiner

METHOD, SYSTEM AND SOFTWARE FOR PROTECTIVE VENTILATION

RELATED APPLICATIONS

This application claims priority to Swedish Patent Application No. 1550671-0 filed May 25, 2015, entitled "Method System and Software for Protective Ventilation", which is hereby incorporated herein by reference in its entirety for all purposes.

FIELD OF THE INVENTION

This invention pertains in general to the field of breathing apparatuses. The invention relates more particularly to methods and systems for ventilating a patient using a fast measurements sequence for determination of the elastic properties of the lungs and for preventing damage to the lungs of a patient being ventilated, as well as to clinical decisions systems preferably including user interfaces of such breathing apparatuses, in particular graphical user interfaces (GUI's) thereof.

BACKGROUND OF THE INVENTION

During the polio epidemic in Copenhagen in 1952, manually controlled ventilation was used to provide adequate gas exchange in patients to normalize oxygen levels, remove carbon dioxide, and thereby save the lives of patients with compromised respiration. Just one year later during a polio epidemic in Stockholm, ventilator treatment was introduced on a large scale to treat not only polio patients but to provide respiratory treatment to patients with respiration compromised by other causes. The focus of mechanical ventilation on normalizing gas exchange lead to the use of large tidal volumes, often over 10-12 ml/kg body weight, along with concomitant high airway pressures. In 1967, increased positive end-expiratory airway pressure (PEEP) was introduced as a method to improve gas exchange. Successively, it was realized that there were side-effects of mechanical ventilation, such as compromising effects on circulation and injury to lung parenchyma by the high pressures and tidal volumes used (barotrauma and volutrauma). Additionally, injury to the lung parenchyma can cause secondary failure in other organs.

A breathing apparatus may be set to provide desired gas exchange in the lungs by adjusting PEEP and tidal volume (VT). Some combinations of PEEP and VT may result in an end inspiratory transpulmonary pressure (PTPEI) that is high enough to cause damage to the lungs. During PEEP treatment, the therapist seeks a reasonable compromise between the risk of lung tissue damage and desired or acceptable gas exchange. An improperly selected ventilator strategy can cause injury to the lung tissue, or Ventilator Induced Lung Injury (VILI). The selection of a PEEP level that provides desired gas exchange without risking damage to the lungs is difficult in many cases and a number of approaches for selecting safe and effective PEEP levels have been used with limited clinical success. Most methods for selecting a PEEP level for respiratory therapy are based on the oxygenation of the patient using PEEP/FIO2 (fraction of inspired oxygen) tables or are applied without knowing whether the individual patient is a responder or non-responder to PEEP. It has recently been shown that there is a direct correlation between the driving pressure of the respiratory system, i.e. the airway pressure variation related to breathing cycle and mortality in acute respiratory distress syndrome (Amato et al. Driving Pressure and Survival in the Acute Respiratory Distress Syndrome. N Engl J Med 2015; 372(8):747-755). However, in accompanying editorial by Loring and Malhotra it was remarked that the authors should have used the transpulmonary driving pressure, i.e. the driving pressure over the lung alone for the analysis, instead of the airway driving pressure, which is the driving pressure of the lung AND the chest wall (Loring, Malhotra. Driving Pressure and Respiratory Mechanics in ARDS. N Engl J Med 2015; 372(8):776-777). The reason for the analysis being based on the combined lung and chest wall driving pressure instead of the lung driving pressure alone is the fact that the conventional method for separation of lung driving pressure demands measurement of esophageal pressure, which is complicated and rarely used in scientific studies and even less in clinical practice. The most common methods to set PEEP are based on measurement of total respiratory system mechanics, i.e. the combined chest wall and lung mechanics (e.g. total elastance), rather than measuring lung mechanics (e.g. lung elastance) separately. Thus, the greatest limitations of existing breathing apparatus and associated ventilation strategies is that they do not provide a way for the user to avoid a strategy that may cause VILI or to ensure that a strategy will not result in an end inspiratory transpulmonary pressure (PTPEI) that is below a predetermined maximum value or a safe transpulmonary driving pressure ($\Delta$PTP). Another drawback of existing systems and methods for ventilation is that, PTP is measured using esophageal pressure as a surrogate for pleural pressure.

WO 2011/157855 A1, which is incorporated herein by reference in its entirety for all purposes, especially equations 1-17 and their descriptions on pages 7-14, discloses that it is possible to calculate an estimated transpulmonary pressure after measuring lung elastance as the ratio of change in end-expiratory airway pressure ($\Delta$PEEP) to change in end-expiratory lung volume ($\Delta$EELV), $\Delta$PEEP/$\Delta$EELV following a PEEP step maneuver. WO 2011/157855 does not disclose clinically applicable measurement sequence systems comprising graphic visualizations based upon calculated values of lung elastance.

During ventilation of a patient clinicians often seek to maintain a certain ventilation strategy for a treatment which is believed particularly advantageous for a ventilated patient. WO 2014/124684 A1, which is incorporated herein by reference for all purposes, in particular FIGS. 3-9 and their corresponding descriptions, discloses a breathing apparatus with a ventilation strategy tool comprising a graphic visualization tool that provides a combination of a target indication one or more ventilation related parameters of a ventilation strategy and a reciprocating animation of parameter(s) relative the target indication, which may be based upon user input. WO 2014/124684 does not disclose calculating values for lung elastance or using such values for avoiding VILI.

There is hitherto no flexible tool to provide clinicians with a status of an on-going ventilation in a clear and easily understandable way when it comes to the crucial point of how the current patient ventilation is related to a chosen ventilation strategy. It would be particularly desirable for such a tool to be adaptable to the status of an on-going ventilation of a patient during the ventilation itself. Also, it would be desired if the tool provided a feedback to the clinician that can be understood from a distance from a breathing apparatus. It would be desired, for instance, to provide a quick overview of a current ventilation strategy to the clinical user. Each ventilation strategy has a target. A quick identification of compliance of an ongoing ventilation with this target to the clinical user would be desired and allow for faster clinical decision taking related to the ventilation strategy. For instance, a patient in an isolation room or during an x-ray examination might not be approached by the clinician with undue burden. Thus, such a tool would be advantageous if it provided the clinician with a current status of a ventilation in relation to a desired strategy, even for a projected outcome of adjustments to clinical ventilation parameters, e.g. in a simulated ventilation. The clinician could thus focus on patient treatment, which in turn is made more effective.

For instance for education of clinicians, it would be advantageous if this tool was provideable without a patient connected to the breathing apparatus, e.g. in a simulated ventilation, e.g. based on a test lung connected to the breathing apparatus. Hence, there is a need for such a tool implemented in a system including a breathing apparatus that can provide the ventilation, and based on adjustments thereof pursues the desired ventilation strategy. Clinical decisions related to the treatment of a ventilated patient might then be facilitated. Based on a target input from a clinical user, the breathing apparatus may automatically adjust remaining ventilation parameters for safe and reliable ventilation ensuring sufficient oxygenation of a connected patient. A corresponding method, software and system are provided. Treatment of the ventilated patient may thus be improved. Cost of care can potentially be reduced by the more effective treatment that can be provided related to the chosen ventilation strategy.

Thus, an improved breathing system for providing a clinical tool providing clear and easily understandable status for an on-going ventilation strategy in relation to a desired outcome thereof would be advantageous. This need and the above-mentioned limitations of the current state of the art are addressed by the current disclosure, wherein the present invention provides an improvement over the state of the art in the field of breathing apparatus and ventilation.

BRIEF SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing systems, breathing apparatus, computer programs, and methods according to the appended patent claims.

The invention is defined in the appended independent patent claims, wherein specific exemplary embodiments are defined in the dependent claims.

In a first aspect, the present disclosure includes a system including a breathing apparatus and a processing unit, where the system is configured to raise a first positive end-expiratory pressure PEEP level to at least a second PEEP level above said first PEEP level, determine an increase in end expiratory lung volume EELV ($\Delta$EELVup) and subsequently lowering said second PEEP level to said first PEEP level, determine a decrease in EELV ($\Delta$EELVdown), calculate a mean change in end-expiratory lung volume between said first PEEP level and said second PEEP level as ($\Delta$EELVup+$\Delta$EELVdown)/2, set a tidal volume to be equal to $\Delta$EELVmean, and calculate a lung mechanics equation relating total lung volume above functional residual capacity (FRC) to transpulmonary pressure (PTP) of a lung connected to said breathing apparatus, at said tidal volume equal to $\Delta$EELVmean.

In a second aspect, the disclosure includes a method of setting a desired value of a ventilation parameter in a breathing apparatus connected to a lung, test lung, model lung or artificial lung. The method comprises calculating a value for PTPEI using said lung mechanics equation calculated by the system of the first aspect and selecting a VT and PEEP based upon said lung mechanics equation.

In a third aspect, the disclosure includes a method of adjusting at least one second ventilation parameter in a breathing apparatus for a ventilation of a connected lung, test lung, model lung or artificial lung based on a target input of a first ventilation parameter from a clinical user. The method includes raising a first positive end-expiratory pressure PEEP level to at least a second PEEP level above said first PEEP level, determining an increase in end expiratory lung volume EELV ($\Delta$EELVup) and subsequently lowering said second PEEP level to said first PEEP level, determining a decrease in EELV ($\Delta$EELVdown), calculate a mean change in end-expiratory lung volume between said first PEEP level and said second PEEP level as ($\Delta$EELVup+$\Delta$EELVdown)/2, setting a tidal volume to be equal to $\Delta$EELVmean, and calculating a lung mechanics equation relating total lung volume above functional residual capacity (FRC) to transpulmonary pressure (PTP) of the lung, test lung, model lung or artificial lung connected to the breathing apparatus, based on said $\Delta$EELVmean between said first PEEP level and said second PEEP level, and adjusting the at least one second ventilation parameter, the at least one second ventilation parameter being at least one of PTPEI, VT and PEEP based on said lung mechanics equation.

In a fourth aspect, the invention is a computer program, preferably embodied on a computer-readable medium, for performing the method of the second or third aspect.

Further embodiments of the invention are defined in the dependent claims, wherein features for the second and subsequent aspects of the invention are as for the first aspect mutatis mutandis.

Protective ventilation, or lung protective ventilation, of patients is thus provided or implementable for both normal and/or injured lungs (e.g. ARDS patients, see below). The clinician can thus focus on patient treatment, which in turn is made more effective. Treatment is provided more reliable and patient safety increased.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which FIGS. 1A and B are examples of V/P graphs that may be used to estimate of $\Delta$EELV between ZEEP/FRC and baseline clinical PEEP.

DETAILED DESCRIPTION OF THE INVENTION

Figure 1:
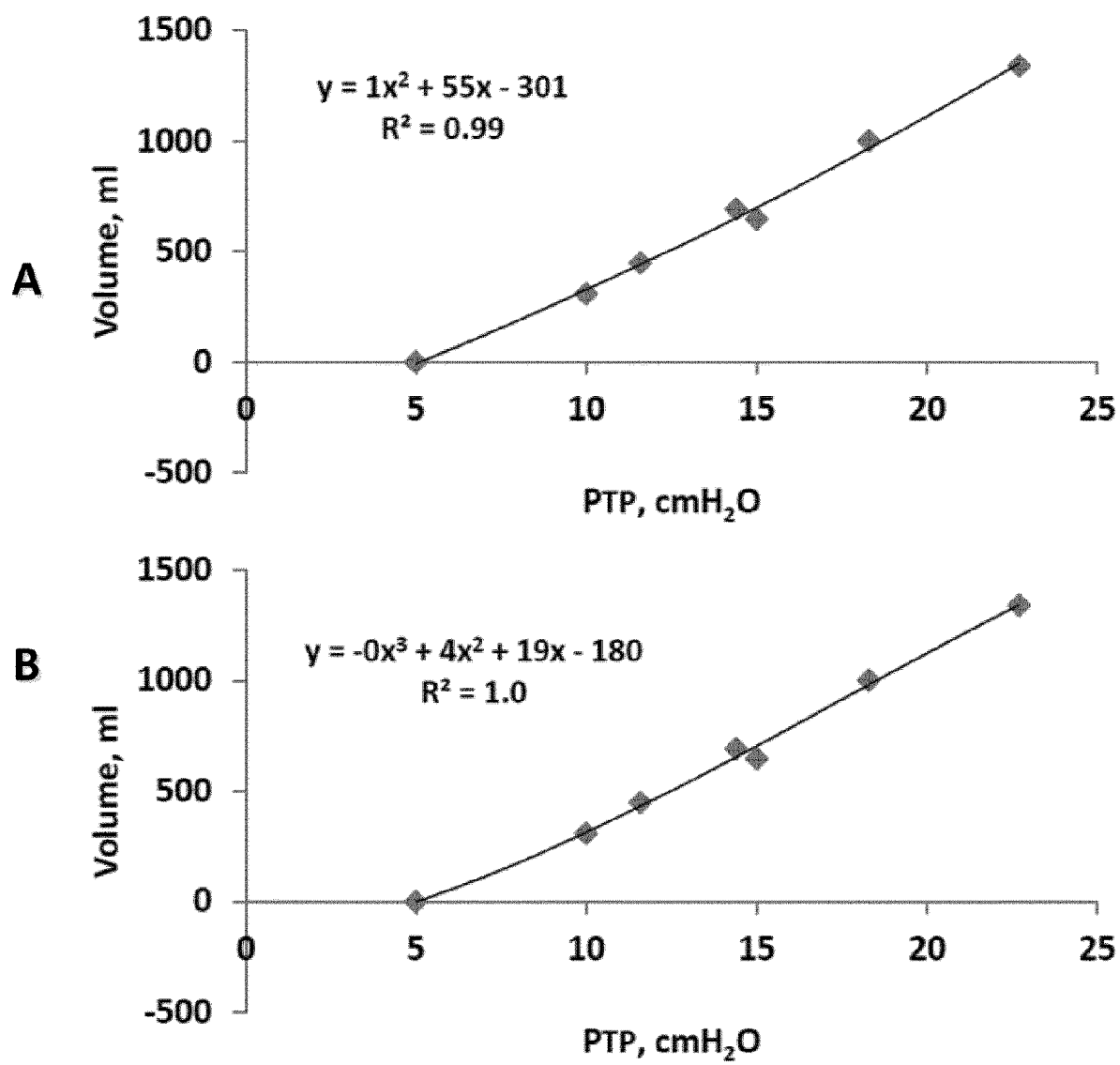

The invention is based, in part, on the discovery that it is possible to obtain a PTP vs. volume curve (P/V curve) for a patient in a way that allows a breathing apparatus system and/or a user of such a system to quickly determine whether or not a selected combination of positive end-expiratory pressure (PEEP) and tidal volume (VT) will result in an end-inspiratory transpulmonary pressure (PTPEI) that is above a pre-determined limit, or a transpulmonary driving pressure ($\Delta$PTP) that is deemed harmful, e.g. to prevent damage to the lungs. The inventors have discovered how to obtain a complete lung P/V curve using one or more PEEP steps, and furthermore, how to obtain it breath-by-breath.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description describes an embodiment applicable to a breathing apparatus and in particular to a respiratory ventilator in use connected to sources of pressurized gas. However, it will be appreciated that the invention is not limited to this application but may be applied to many other breathing apparatuses, including for example fan driven breathing apparatuses. The embodiment described is a breathing apparatus in form of an intensive care respiratory ventilator. However, other embodiments may comprise anaesthetic vaporizers, breathing circles, etc. connected to the breathing apparatus without deviating from the invention. The invention is suited for all groups of patients, including adult/paediatric patients or neonatal patients.

An example of a breathing apparatus can be found in WO 2011/157855, e.g. in relation to FIG. 1, which is hereby incorporated herein by reference in its entirety for all purposes.

Determination of End-Expiratory Lung Volume Changes, $\Delta$EELV

An incremental PEEP trial results in a "PEEP induced" inflation of the lungs. The increase in EELV following a PEEP increase can be calculated as the difference in absolute lung volume (EELV) between two PEEP levels, where the EELV at each PEEP level is determined by a dilution method or any method for determination of the absolute lung volume, but due to the imprecision and slowness of such measurements they are unsuitable for the purpose of the present invention. The change in EELV can also be traced by electric impedance tomography (EIT) but such measurements require the careful calibration of the EIT signal by the ventilator spirometer. Thus, a direct measurement of $\Delta$EELV by the ventilator pneumotachograph/spirometer is preferred for a rapid and accurate determination of $\Delta$EELV.

Lung Elastance (EL) and Transpulmonary Pressure (PTP) Determination

The conventional method for determining EL and PTP is by using esophageal pressure measurements as a surrogate for pleural pressure, where PTP is the difference in tidal airway pressure and tidal esophageal pressure. Measurement of esophageal pressure is time consuming and there is no consensus on the interpretation of the absolute values or values in relation to atmospheric pressure. As a consequence, only tidal variations in esophageal pressure are used. Also, the measurement of tidal esophageal pressure poses several obstacles. Measurements are sensitive to the filling of the balloon of the measurement catheter and position of the catheter. Several other factors have a detrimental effect on measurement results and all together precision is low. Thus, esophageal pressure measurements can be used for calculation of a lung P/V curve in the individual patient during a PEEP trial, but they are not preferred.

Total respiratory system elastance (ETOT) is the difference in end-inspiratory airway plateau pressure and the end-expiratory airway pressure ($\Delta$PAW) divided by the tidal volume (VT), $\Delta$PAW/VT. Chest wall elastance (ECW) is the difference in end-inspiratory esophageal plateau pressure and the end-expiratory esophageal pressure ($\Delta$PES) divided by the tidal volume (VT), $\Delta$PES/VT. Lung elastance (EL) is the difference between total respiratory system elastance and chest wall elastance, ETOT-ECW. Tidal transpulmonary pressure variation ($\Delta$PTP) is calculated as EL×VT. $\Delta$PTP of a tidal volume equal to the change in end-expiratory lung volume (VT=$\Delta$EELV) is calculated as EL×$\Delta$EELV.

Determination of the Complete Lung P/V Curve from Zero End-Expiratory Airway Pressure (ZEEP) and at Functional Residual Capacity (FRC), ZEEP/FRC to End-Inspiration of a Highest PEEP Level, by Lung Barometry The basic Lung Barometry concept is that lung elastance, EL, is equal to the change in PEEP divided by the corresponding change in end-expiratory lung volume, $\Delta$PEEP/$\Delta$EELV, herein denominated as "Lung Barometry". Thus, the determination of $\Delta$EELV is an inherent part of a method involving Lung Barometry, determination of parameters based on it, or further processed data generated from its result. Airway pressure measurements are very precise and modern ventilators keep set PEEP levels constant. The $\Delta$EELV following a PEEP change can be determined by the cumulative difference between inspiratory and expiratory tidal volumes (VTi-e) between two steady state PEEP/EELV levels. The change in $\Delta$EELV following a PEEP change is a slow process with a duration of minutes, up to an hour. The measurement precision is hampered by the fact that the offset between inspiratory and expiratory tidal volume changes slightly when changing PEEP level. The change in offset is usually some few ml and is not a problem as long as the cumulative VTi-e difference is determined during a period of less than a minute. However, with a fairly normal breathing frequency of 20/min, a change in offset of as little as 2 ml/breathing cycle will cause an unacceptable error in ΔEELV if measurements of a duration of more than one-two minutes is used (e.g. FIG. 4B). The inventors of the present invention have realized that a build-up of a new PEEP/EELV equilibrium is considerably slower during a PEEP increase as compared to a PEEP decrease. Even after a PEEP increase that has lasted for several minutes, where ΔEELV cannot be determined adequately, ΔEELV after an ensuing PEEP decrease back to baseline will be almost complete within two minutes. Thus, ΔEELV between two PEEP levels can be determined with high precision also after a long duration of the PEEP increase preceding the PEEP step down as the baseline VTi-e offset can be applied for calculation of the ΔEELV during the PEEP down procedure. The determination of EL by Lung Barometry only demands a change in PEEP and a spirometric determination of the resulting ΔEELV. This is a very simple and precise method, which is much more suitable than esophageal measurement-based for determination of the lung P/V curve during a PEEP trial.

Chest wall elastance is linear and constant when changing PEEP, but lung elastance is normally non-linear, including both lower and upper inflection points on the lung P/V curve. As a consequence, the total respiratory system P/V curve, the sum of the lung and chest wall P/V curves will show the same non-linearity as the lung P/V curve. Thus, it is of outmost importance that total respiratory system elastance and lung elastance is determined for the same lung volume range i.e. ΔEELV between the two PEEP levels should equal to the tidal volume from the low PEEP level for an adequate calculation of chest wall elastance, which is used to establishing the complete lung P/V curve and the continuous breath-by breath calculation of transpulmonary driving pressure, ΔPTP. Thus, when starting a lung elastance measurement sequence, i.e. increasing PEEP and determining ΔEELV, it is advisable to increase PEEP by a default value of ≈70% of the airway driving pressure (ΔPAW), as the transpulmonary driving pressure on average, based on data of several studies (Gattinoni et al. AJRCCM 1998, Pelosi et al. AJRCCM 1995, Lundin et al. AAS 2014, Garnero et al. MA 2014), is around 70% of the airway driving pressure. However, in the individual patient, the transpulmonary driving pressure may vary between 40% and 90% of the airway driving pressure. As a consequence, the increase in PEEP may result in a ΔEELV value that is not equal to the tidal volume. After PEEP is lowered back to baseline, the tidal volume is adjusted to be equal to ΔEELV and total respiratory system elastance is determined for this tidal volume (=ΔEELV).

If baseline PEEP level is so high that it is clinically impossible to make a further increase in PEEP, the measurement sequence can be performed in reverse, i.e. PEEP is first decreased during a minute and then increased to baseline level.

If ΔEELV is so low or so high, that it is not clinically feasible to decrease or increase the tidal volume to such a level, a new measurement sequence with a higher or lower ΔPEEP should be implemented.

Total respiratory system elastance is determined as ΔPAW/VT=ΔEELV and lung elastance is determined as ΔPEEP/ΔEELV. The corresponding chest wall elastance is determined as (ΔPAW/VT=ΔEELV)−(ΔPEEP/ΔEELV).

Total respiratory system elastance (ETOT) is the difference in end-inspiratory airway plateau pressure and the end-expiratory airway pressure (ΔPAW) divided by the tidal volume (VT), ΔPAW/VT. Chest wall elastance (ECW) is the difference between total respiratory system elastance and lung elastance, ETOT-EL, where ETOT is determined using a tidal volume equal to ΔEELV. Lung elastance (EL) is the ratio of change in end-expiratory airway pressure (ΔPEEP) to the corresponding change in end-expiratory lung volume (ΔEELV), ΔPEEP/ΔEELV. ΔPTP of a tidal volume equal to the change in end-expiratory lung volume (VT=ΔEELV) is by definition equal to the change in end-expiratory airway pressure (ΔPEEP).

The Basic Measurement Algorithm—Example

Start from a steady state clinical PEEP level.

Increase PEEP by 70% of the ΔPAW. The PEEP increase is preferably around 70% but may be greater or less than 70%, for example 30%, 40%, 50%, 60%, 80%, 90%, or 100%.

Determine the increase in EELV (ΔEELVup) as the cumulative difference between inspiratory and expiratory tidal volumes during ≈1 minute, e.g. 30, 40, 45, 50, 55, 60, 65, 70, or 75 seconds. Return to baseline PEEP ≈2 minutes after the increase in PEEP, for example 90, 100, 110, 120, 130, 140, or 150 seconds.

Determine the decrease in EELV (ΔEELVdown) as the cumulative difference between inspiratory and expiratory tidal volumes during ≈1 minute.

Calculate the mean ΔEELV as (ΔEELVup+ΔEELVdown)/2.

Set the tidal volume to mean ΔEELV.

Determine total respiratory system elastance ETOT as ΔPAW/VT=meanΔEELV.

Calculate lung elastance (EL) as ΔPEEP/ΔEELVmean.

Calculate chest wall elastance (ECW) as the difference between total respiratory system elastance and lung elastance, ECW=ETOT−EL.

Calculate the ratio EL/ETOT and calculate the ratio of EL to ETOT at the higher PEEP level as (ETOTHP−ECWBL)/ETOTHP.

Example—Determining PTP Using Basic Lung Barometry

As the chest wall complex reacts as a hydraulic entity during controlled ventilation, chest wall elastance is linear. As the chest wall complex is not acting as an elastic expandable structure, but rather like a weight that is displaced during a PEEP change, chest wall elastance is mainly constant during PEEP changes. During volume control ventilation, inspiratory flow is constant and the pressure drop between the proximal end of the tube and the alveoli can be regarded as constant, i.e. the difference between peak airway pressure and plateau airway pressure measured during the end-inspiratory pause (PAWpeak-plateau) is also at hand already at start of inspiration. As a consequence, the alveolar driving pressure (PALV) can be calculated as momentary PAW-PAWpeak-plateau and the transpulmonary driving pressure can be calculated continuously during inspiration, as momentary PALV minus momentary tidal volume times chest wall elastance.

The end-expiratory PTP at baseline (PTPEEBL), clinical PEEP and baseline lung volume of zero is equal to the end-expiratory airway pressure (PEEP): PTPEEBL=PAWEEBL.

The end-expiratory PTP at the higher PEEP level (PTPEEHP) and a lung volume above baseline equal to ΔEELVmean is equal to the PEEP at the higher PEEP level: PTPEEHP=PAWEEHP.

The end-inspiratory PTP at baseline PEEP and a lung volume above baseline EELV equal to VTBL is PTPEIBL=PTPEEBL+ΔPAW×VTBL−ECWBL×VTBL.

The end-inspiratory PTP at the higher PEEP level and a lung volume above baseline equal to ΔEELVmean+VTHP is PTPEIHP=PTPEEHP+ΔPAWVTHP−ECWBL×VTHP.

ECW remains mainly constant when changing PEEP.

Example—Estimation of ΔEELV Between ZEEP/FRC and Baseline EELV

Data of PTP at end-expiration and end-inspiration at baseline and the higher PEEP level is plotted versus corresponding EELV data. The best fit polynomial curve of the second and the third degree curve are plotted. The equation for the best fit curves are solved for zero PTP, which gives the mean volumes where the curves intersect with the volume axis at zero PTP. This estimated volume, ΔEELV0-BL, is added to all the previous EELV values, which means that EELVBL is equal to ΔEELV0-BL and that end-inspiratory lung volume at baseline lung volume is ΔEELV0-BL+VTBL. EELV at the high PEEP level is ΔEELV0-BL+ΔEELVBL-HP and the end-inspiratory lung volume at the high PEEP level is ΔEELV0-BL+ΔEELVBL-HP+VTHP.

The Extended Lung Barometric Measurement Algorithm—Example

The extended algorithm contains two consecutive PEEP steps, HP1 and HP2, still starting from a baseline clinical PEEP, but now reaching a higher lung volume and PTP.

The first increased PEEP level (PEEPHP1) is maintained only for a minute and ΔEELVBL-HP1up is determined as described for the basic algorithm. The size of the second PEEP step is predicted as the difference in end-inspiratory plateau airway pressure between the high and the baseline PEEP levels, PAWEIHP1-PAWEEBL. ΔEELVHP1-HP2up is determined as described for the basic algorithm.

The second increased PEEP level (PEEPHP2) is maintained for a minute before returning PEEP to HP1. ΔEELVHP1-HP2 down and mean ΔEELVHP1-HP2up-down are determined as described for the basic algorithm.

EL between PEEPHP1 and PEEPHP2 is determined as the difference in PEEP between HP2 and HP1 divided by the mean change in EELV between HP2 and HP1, ΔPEEPHP1-HP2/ΔEELVHP1-HP2.

ETOT at HP2 is calculated as ΔPAWHP2/VTHP2.

ECW at HP2 is calculated as ETOTHP2-ELHP2.

A minute after lowering PEEP from HP2 to HP1, PEEP is lowered to baseline PEEP level. During the first minute after decreasing PEEP, ΔEELVBL-HP1down and meanΔEELVBL-HP1 are determined as described for the basic algorithm.

The tidal volume is set to mean ΔEELVBL-HP1.

ETOT is determined as ΔPAWBL/VT=meanΔEELVBL-HP1.

EL is calculated as ΔPEEP/ΔEELVmeanBL-HP1.

ECW is calculated using ECWBL=ETOTBL-ELBL.

The ratio of EL to ETOT at baseline is calculated: ELBL/ETOTBL.

The ratio of EL to ETOT at PEEPHP1 is calculated: ELHP1/ETOTBP1.

The ratio of EL to ETOT at the PEEPHP2 is calculated: (ETOTHP2-ECWHP1)/ETOTHP2.

Example—Transpulmonary Pressure by Extended Lung Barometry

ECW is assumed to remain essentially constant when changing PEEP.

The end-expiratory PTP at baseline (PTPEEBL), clinical PEEP and baseline lung volume of zero is equal to the end-expiratory airway pressure (PEEP); PTPEEBL=PAWEEBL.

The end-expiratory PTP at the higher PEEP level (PTPEEHP1) and a lung volume above baseline equal to ΔEELVmeanBL-HP1 is equal to the PEEP at PEEPHP1; PTPEEHP1=PAWEEHP1.

The end-expiratory PTP at the highest PEEP level (PTPEEHP2) and a lung volume above baseline equal to ΔEELVmeanBL-HP1+ΔEELVmeanHP1-HP2 is equal to the PEEP at PEEPHP2: PTPEEHP2=PAWEEHP2

The end-inspiratory PTP at baseline PEEP and a lung volume above baseline EELV equal to VTBL is PTPEIBL=PTPEEBL+ΔPAWVTBL−ECWBL×VTBL The end-inspiratory PTP at PEEPHPI and a lung volume above baseline equal to ΔEELVmean+VTHP is PTPEIHP1=PTPEEHP1+ΔPAWVTHP1−ECWHP1×VTHP1

The end-inspiratory PTP at PEEPHP1 and a lung volume above baseline equal to ΔEELVmean+VTHP is PTPEIHP2=PTPEEHP2+ΔPAWVTHP2−ECWHP2×VTHP2

Example—Estimation of ΔEELV Between ZEEP/FRC and Baseline EELV by Extended Lung Barometry The lung volume between the low PEEP level and functional residual volume (FRC) at zero PEEP can be determined by a short decrease of PEEP to 0 cmH2O for 5-10 breaths, a duration similar to that of a short disconnection of the breathing system, such as during a suctioning procedure. If this is not regarded as a clinically safe procedure, this volume can be estimated by extrapolation of the single lung P/V curve between the low PEEP/EELV level and ZEEP/FRC. FIG. 1 shows how EELV between a baseline PEEP and ZEEP/FRC can be determined without lowering PEEP to zero. Data of PTP at end-expiration and end-inspiration at baseline and PEEPHP1 and PEEPHP2 are plotted versus corresponding EELV data. A best fit polynomial of the second and third degree curve is plotted. The equations for the best fit curves are solved for zero PTP, which gives the mean volume where the curve intersects with the volume axis at zero PTP. This estimated volume, ΔEELV0-BL, is added to all the previous EELV values, which means that EELVBL is equal to ΔEELV0-BL and that end-inspiratory lung volume at baseline lung volume is ΔEELV0-BL+VTBL. EELV at PEEPHP1 is ΔEELV0-BL+ΔEELVBL-HP and the end-inspiratory lung volume at the high PEEP level is ΔEELV0-BL+ΔEELVBL-HP1+VTHP1. The end-expiratory lung volume at PEEPHP2, EELVHP2 is ΔEELV0-BL+ΔEELVBLHP1+ΔEELVHP1-HP2 and the end-inspiratory lung volume at the high PEEP level is ΔEELV0-BL+ΔEELVBL-HP2+VTHP2. FIGS. 1A and B are graphs showing estimations of ΔEELV between ZEEP and baseline clinical PEEP. FIG. 1A shows a polynomial second degree best fit curve equation for the PTP/V points of the PEEP trial. FIG. 1B shows a polynomial third degree best fit curve equation for the PTP/V points of the PEEP trial. The mean of the values for the intercepts of the curves and the y-axis are used. For FIGS. 1A and B the mean of the values is (301+180)/2=240 ml.

Example—Identification of Inflection Points/Zones

Figure 2:
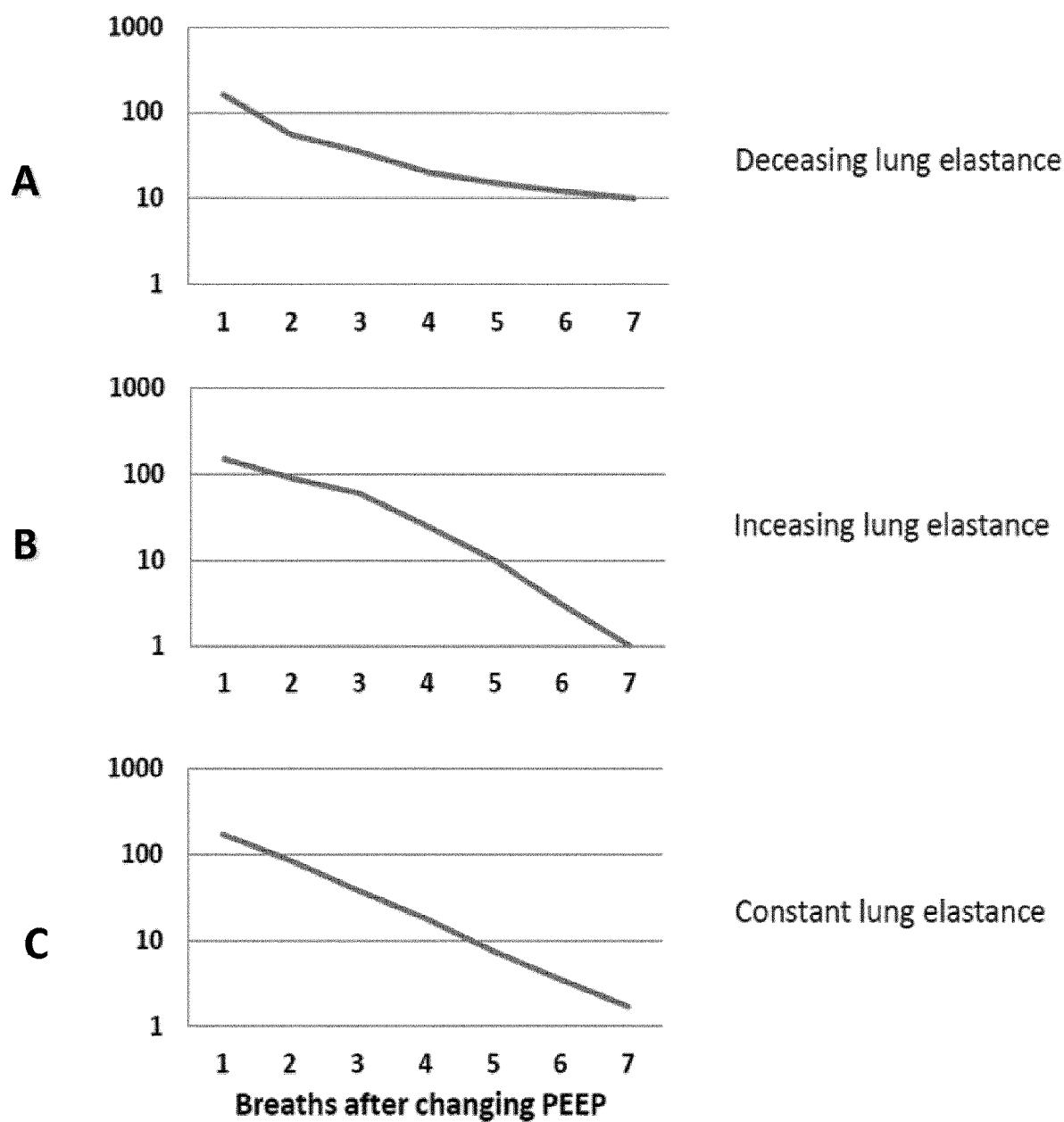
FIGS. 2A-C are graphs of breath by breath change in EELV after a PEEP change plotted on a logarithmic scale.

The establishment of a new P/V equilibrium after increasing PEEP involves multiple breaths, where the lung volume increase decreases breath-by-breath until a new steady state is established. If the volume increase (DEELV) of each breath is plotted on a logarithmic volume scale, an upwards convex (increasing lung elastance) or concave (decreasing lung elastance) or linear slope of lung elastance can be identified for the lung volume between the two PEEP levels. FIGS. 2A-C are examples of log EELV vs. breath graphs that correspond to decreasing, increasing, and constant EL between two different PEEP levels.

Figure 3:
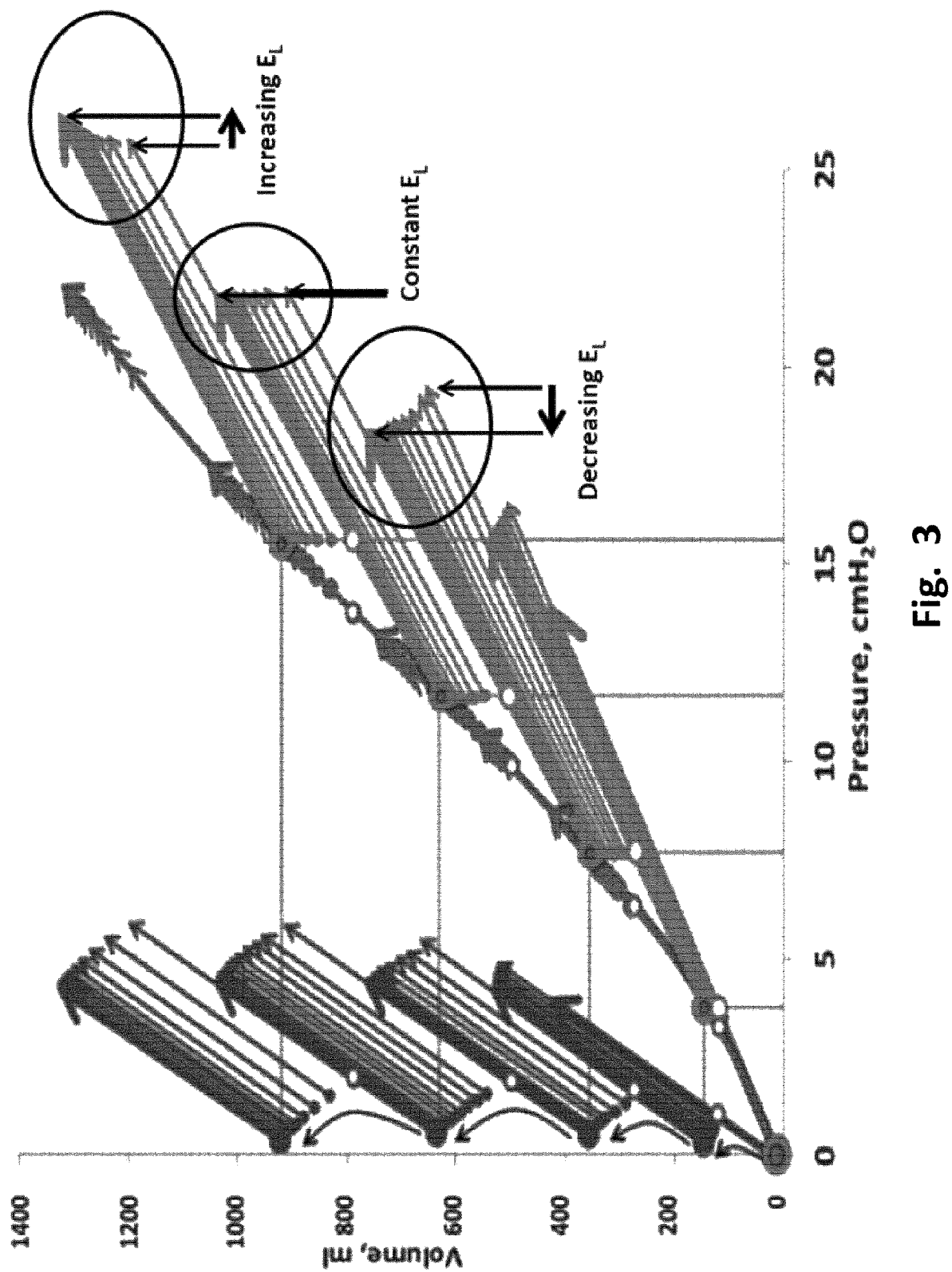
FIG. 3 is an example of a graph showing breath by breath airway, esophageal and transpulmonary pressure volume curves during a PEEP trial from ZEEP to 16 cmH2O.

Identification of Non-Linearity at a Volume Range Between the End-Inspiratory Lung Volume (EILV) of Two PEEP Levels Using the breath by breath end-inspiratory plateau airway pressure (PAWEI), an increasing EL is reflected in an increasing PAWEI after the first breath after PEEP is increased. If the PAWEI decreases, EL decreases. If PAWEI is constant, EL is constant at the highest volume levels. FIG. 3 shows an example of a type of graph that can be used to identify non-linearity in a volume range between the EILV at two PEEP levels. Breath by breath airway, esophageal and transpulmonary pressure volume curves during a PEEP trial from ZEEP to 16 cmH2O are shown. The progress of the PAWEI is circled. During PEEP change from 4 to 8 cmH2O, PAWEI decreases breath by breath, indicating a decreasing EL. During PEEP change from 8 to 12 cmH2O PAWEI remains mainly constant, indicating an unchanging EL. During PEEP change from 12 to 16 cmH2O PAWEI increases breath by breath, indicating an increasing EL (overdistension).

Example—Lung Barometric Measurement Display

When a measurement procedure is intended to start, a measurement display appears on the screen.

Figure 4:
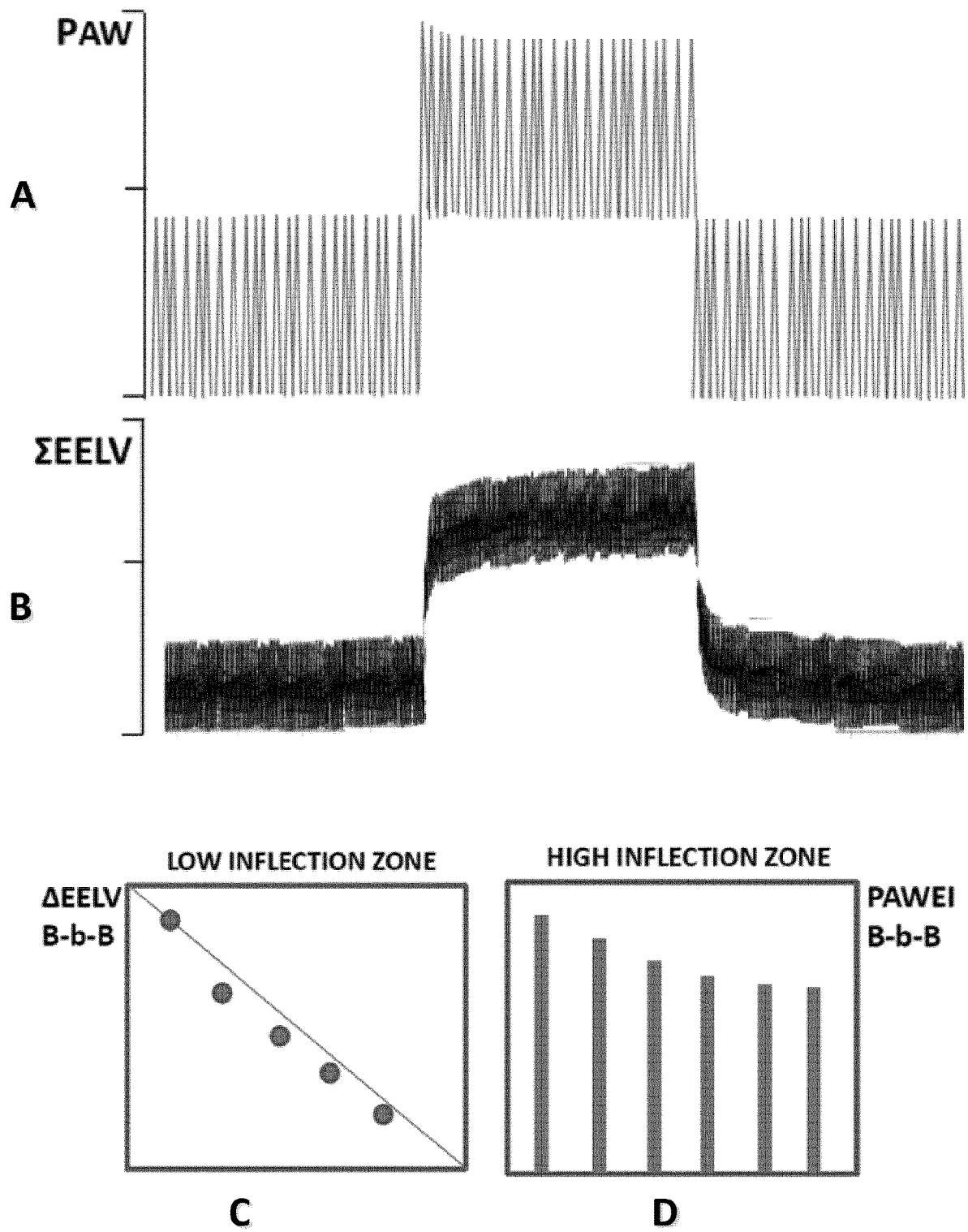
FIGS. 4A and B are graphical displays of airway pressure and EELV measurements breath-by-breath DEELV, measurements.
FIGS. 4C and D are graphic displays of breath-by-breath changes in EELV for low inflection and high inflection zones.

Baseline airway pressures and tidal volumes are presented and steady state is determined. When PEEP is increased, the breath by breath increase in EELV is shown on a logarithmic scale to identify non-linearity, i.e. increase or decrease in EL between two PEEP levels (e.g. FIGS. 2A-C). Additionally, the cumulative increase in EELV may be displayed breath by breath and the ΔEELVup result is displayed (FIG. 4C). FIGS. 4A and B show an illustrative example of such a display in which EL is 70 ml/cmH2O, ΔPTP/ΔPAW at PEEP=5 cmH2O is 0.77, ΔPTP/ΔPAW at PEEP=15 cmH2O is 0.65, ΔPEEPup and ΔPEEPdown are each 10 cmH2O, ΔEELVup is 680 ml, and ΔEELVdown is 720 ml.

The PAWEI may additionally be displayed breath by breath on an enlarged scale to identify increasing or decreasing EL at the end-inspiratory lung-volume level. PEEP is lowered and, after about 2 minutes, the ΔEELVdown and the mean of ΔEELVup and ΔEELVdown is shown and EL (ΔPEEP/ΔEELVmean) may be displayed. The ratio of ΔPTP/ΔPAW for baseline PEEP level and for the higher PEEP level may be displayed.

Examples—Decision Support and Monitoring Display

The ratio of lung elastance to total respiratory system elastance (EL/ETOT) is an indicator whether a PEEP increase will result in more favorable lung mechanics (more compliant lung) or not, i.e. whether the patient is a PEEP responder or not. A positive PEEP response is more likely in patients where the chest wall has a great impact on respiratory system elastance. Thus, the lower the EL/ETOT (0.4-0.8), the more likely it is that lung mechanics will improve (lowered lung elastance) and the higher (>0.8) the less likely is a positive response to PEEP. The EL/ETOT ratio can be determined as (ΔPEEP/ΔEELV)/(ΔPAW/VT=ΔEELV) or alternatively as the ratio of the first expiration (after increasing PEEP) end-expiratory volume increase (VFirstexp) divided by ΔEELV, as EL=ΔPEEP/ΔEELV and ETOT=ΔPEEP/VFirstexp.

Figure 5:
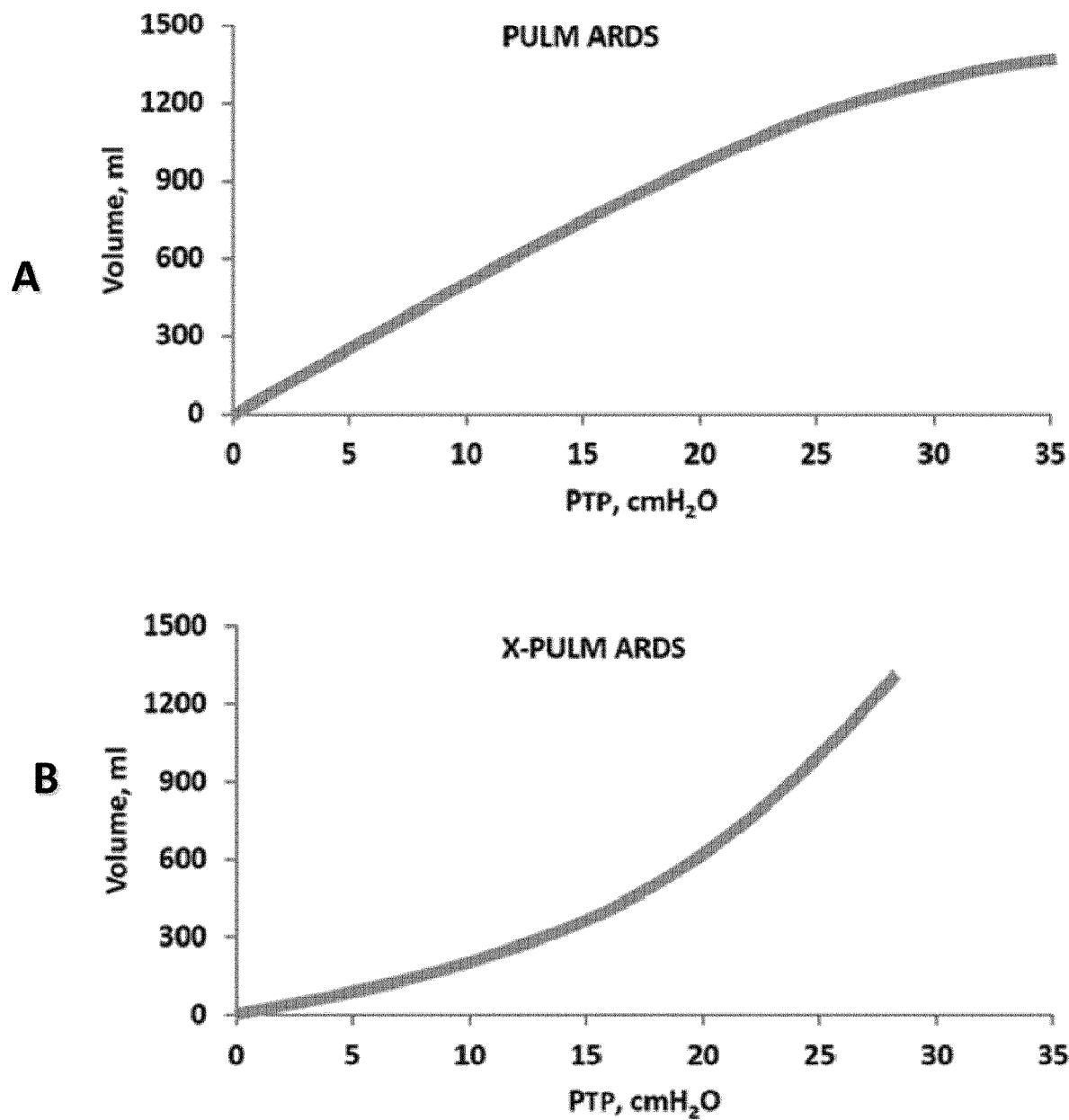
FIGS. 5A and B are examples graphs of complete estimated lung P/V curves corresponding to pulmonary ARDS and extrapulmonary ARDS, respectively.

The EL/ETOT ratio is equal to the ratio of transpulmonary driving pressure to total respiratory system (airway) driving pressure (ΔPTP/ΔPAW). The lower the ΔPTP/ΔPAW ratio (0.4-0.8), the more is the lung protected by the chest wall, i.e. more of the airway driving pressure is "buffered" by the chest wall and the higher the ΔPTP/ΔPAW (>0.8) the more exposed is the lung to the airway driving pressure The complete lung VL/PTP (or PTP/VL) curve with estimated ZEEP/FRC may be displayed, in which PTPEE is equal to PEEP. FIGS. 5A and B are examples graphs of complete estimated lung P/V curves corresponding to pulmonary acute respiratory distress syndrome (ARDS) and extrapulmonary ARDS, respectively. These curves may be generated from a single PEEP increase-decrease cycle or more preferably an extended PEEP cycle in which PEEP is increased in two steps followed by PEEP decrease in two steps. Using an equation for the best fit of the lung P/V curve, decision support is possible.

Example—Pulmonary ARDS

Figure 6:
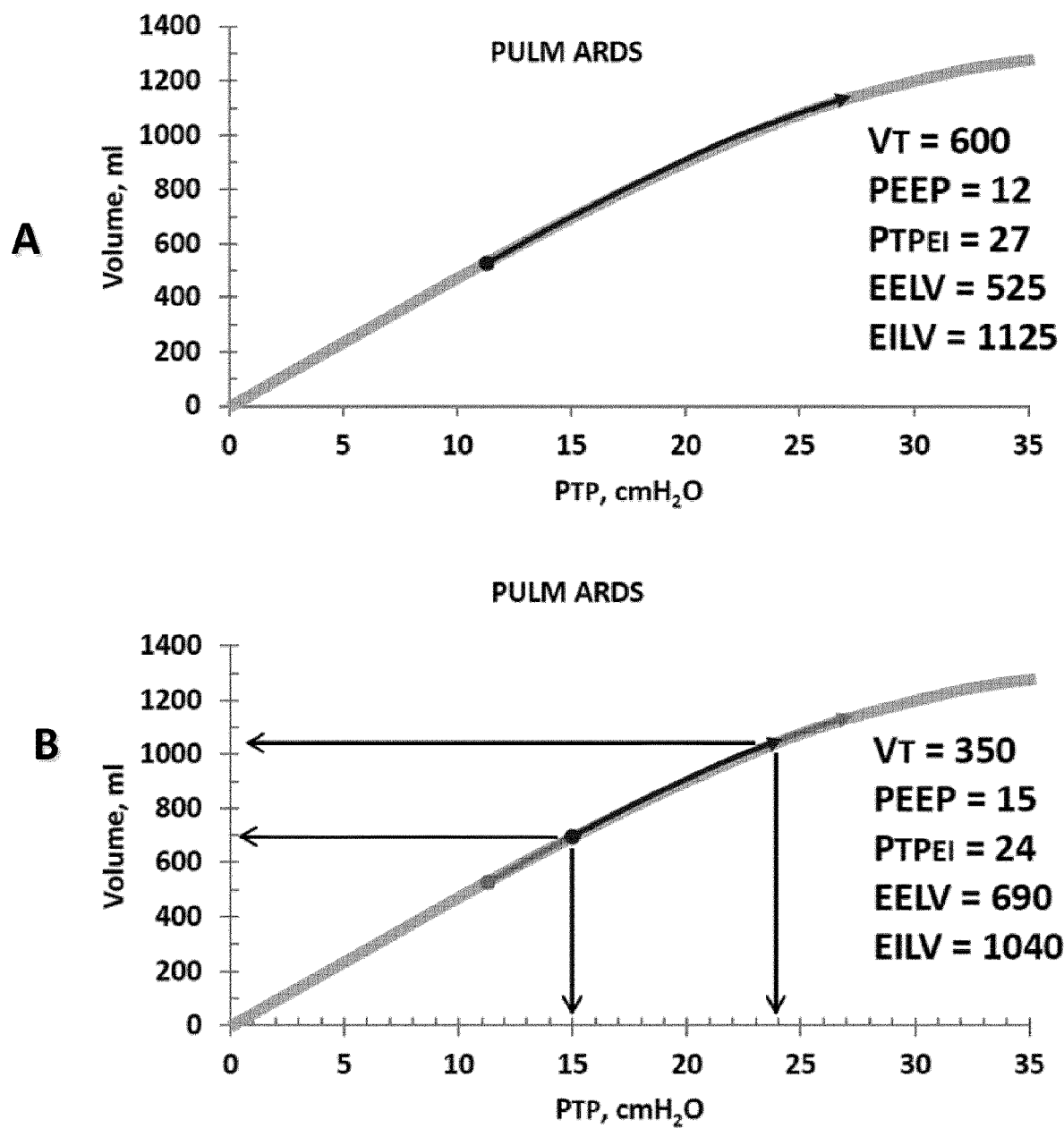
FIG. 6A is graph of the complete PTP/V curve in a pulmonary ARDS patient.
FIG. 6B is the same graph as FIG. 6A including system suggested PEEP and tidal volume settings that result in an end-inspiratory PTP that is below a predetermined maximum level.

The following example corresponds to complete estimated lung P/V curves shown in FIGS. 6A and B for pulmonary ARDS. Using the equation for the best fit lung P/V curve (y=0.0×3+0.8×2+34), and the fact that the end-expiratory PTP changes as much as PEEP (PAWEE) is changed, this display provides information that makes decision support readily available. In this case of pulmonary ARDS, an injurious end-inspiratory PTP level of 27 at PEEP 12 can be identified. The corresponding end-expiratory and end-inspiratory lung volume levels (above FRC) are 525 and 1125 ml. If oxygenation is inadequate, a suggested increase in PEEP level to 15 cmH2O with an increase in EELV from 525 to 690 ml, to improve oxygenation can be combined with a reduction of tidal volume from 600 to 350 ml, resulting in an end-inspiratory lung volume to 1040 ml and a lowered end-inspiratory PTP to 24 cmH2O, slightly below the upper inflection point.

Example—Extrapulmonary ARDS

Figure 7:
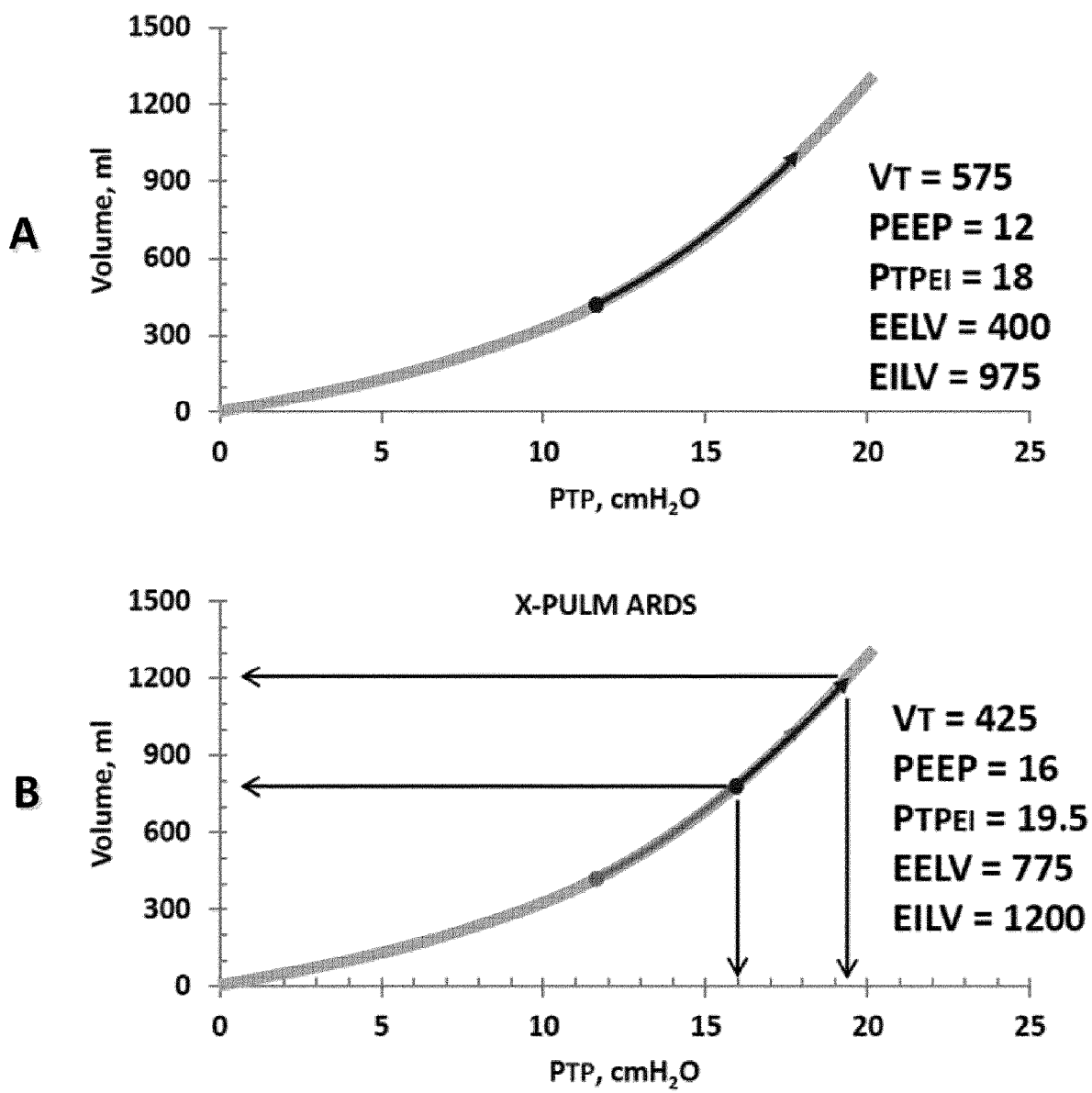
FIG. 7A is graph of a complete PTP/V curve in an extrapulmonary ARDS patient.
FIG. 7B is the same graph as 7A including system suggested PEEP and tidal volume that result in an end-inspiratory PTP that is below a predetermined maximum level.
Figure 8:
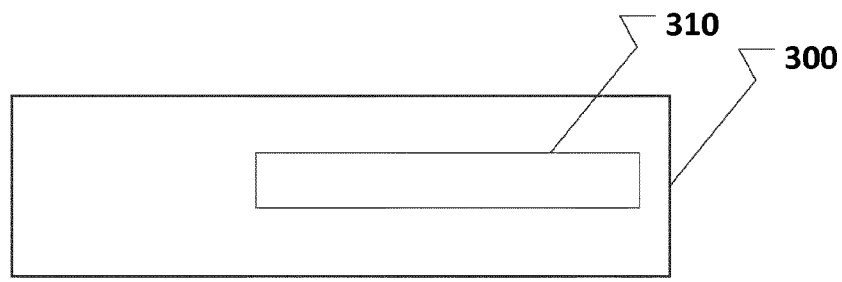
FIG. 8 is a schematic illustration of a breathing apparatus 300 including a control unit 310.
Figure 9:
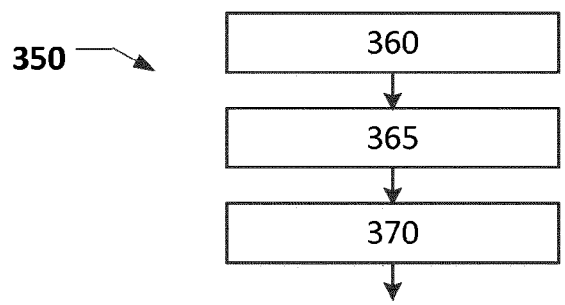
FIG. 9 is a flowchart illustrating an example of a method 350.

The following example corresponds to complete estimated lung P/V curves shown in FIGS. 7A and B for pulmonary ARDS. Using the equation for the best fit lung P/V curve (y=−0.0×3+2.5×2+36) and the fact that the end-expiratory PTP changes as much as PEEP (PAWEE) is changed, this display provides information that makes decision support readily available. In this case of extrapulmonary ARDS, the PTPEI level of 18 cmH2O at PEEP 12 can be identified. The corresponding end-expiratory and end-inspiratory lung volume levels (above FRC) are 400 and 975 ml. If oxygenation is inadequate, a suggested increase of PEEP level to 16 cmH2O with an increase in EELV from 400 to 775 ml can be combined with a reduction of tidal volume from 575 to 425 ml, resulting in an end-inspiratory lung volume to 1200 ml and an end-inspiratory PTP only 1.5 cmH2O higher than before, i.e. 19.5 cmH2O and, well below a possible risk level (pre-determined maximum PTP) of 24 cmH2O. The pre-determined maximum PTP may be higher or lower than 24 cmH2O as determined by a user (e.g. a clinician or respiratory therapist).

Example—Measurement Sequence and Complete Lung P/V Calculation Procedure

Increase PEEP from baseline clinical value and determine the increase in EELV, ΔEELVup.

Decrease PEEP to baseline level and determine the decrease in EELV, ΔEELVdown.

Calculate the mean ΔEELVup and down, ΔEELVmean.

Set tidal volume equal to ΔEELVmean.

Determine respiratory system elastance, ETOT as PAWEIplateau/VT=ΔEELVmean.

Determine lung elastance, EL, as ΔPEEP/ΔEELVmean.

Determine chest wall elastance, ECW as ETOT-EL.

Determine PTPEI at baseline PEEP as baseline PAWEIBL−ECW×VT.

Determine PTPEI at increased PEEP as PAWEIHP1−ECW×VT.

Plot PEEPBL, PEEPHP1, PTPEIBL and PTPHP1 versus corresponding lung volume.

Determine the best fit curve equation (polynomial, second and/or third degree) of PTP/V points.

Use the equation for decision support (see below).

For further improvement in the establishing of the complete lung P/V curve and quantification of non-linearity of the curve, i.e. lower and upper inflection points, the lung P/V curve from end-expiration at the low PEEP level to end-inspiration of the high PEEP level can be determined in analogy with the calculation of the breath-by-breath transpulmonary driving pressure described above (see 3a). The lung P/V curve of the low PEEP level is calculated from the airway P/V curve of the tidal volume equal to ΔEELV at the end of the measurement sequence using chest wall elastance value calculated when the tidal volume is equal to the ΔEELV. The lung P/V curve of the high PEEP level is calculated similarly using the chest wall elastance value calculated when the tidal volume is equal to the ΔEELV.

The low and the high PEEP level lung P/V curves have a common transpulmonary pressure/volume point at end-expiration of the high PEEP level and end-inspiration of the low PEEP level. The two lung P/V curves form a single lung P/V curve from end-expiration at the low PEEP to end-inspiration at the high PEEP level.

This separate lung P/V curve (SLPVC) can be displayed on the ventilator screen with extrapolated or measured lung volume starting from FRC/ZEEP. As the original innovation is based on the finding that end-expiratory airway pressure is equal to end-expiratory transpulmonary pressure, the current tidal lung P/V curve, the transpulmonary driving pressure/volume can be displayed continuously on the SLPVC at the correct lung volume range. As a change in PEEP or tidal volume occurs along the SLPVC, the effect of such changes on the tidal lung P/V curve and transpulmonary driving pressure can be predicted and used as decision support for the clinician.

Further decision support concerning selection of PEEP is offered by EL/ETOT ratio, where ratios between 0.4-0.8 indicates that response to a PEEP increase can be expected to be positive (improved lung mechanics, i.e. more compliant lung tissue).

Also, the ΔPTP/ΔPAW ratio indicates how much of the airway pressure that is directly targeting the lung tissue, ratios >0.8 indicating high risk of lung tissue damage.

A change over time of respiratory system mechanics will result in the tidal lung P/V curve being displaced from the SLPVC, informing the clinician that a new measurement sequence should be performed (similar to a calibration procedure of a pulse contour cardiac output measurement).

The systems and methods described herein may be embodied by a computer program or a plurality of computer programs, which may exist in a variety of forms both active and inactive in a single computer system or across multiple computer systems. For example, they may exist as software program(s) comprised of program instructions in source code, object code, executable code, or other formats for performing some of the method steps. Any of the above may be embodied on a computer readable medium, which includes storage devices and signals in compressed or uncompressed form. The term "computer" refers to any electronic device comprising a processor, such as a general-purpose central processing unit (CPU), a specific purpose processor, or a microcontroller. A computer is capable of receiving data (an input), performing a sequence of predetermined operations on received data, and producing a result in the form of information or signals (an output) resulting from the predetermined operations.

The system includes for instance a breathing apparatus 300 and a processing unit 310. The processing unit 310 is for instance configured to raise a first positive end-expiratory pressure PEEP level to at least a second PEEP level above the first PEEP level and subsequently lowering the second PEEP level to the first PEEP level. The processing unit 310 is for instance further configured to adjust the tidal volume to be equal to the change in end-expiratory lung volume and calculate a lung mechanics equation relating total lung volume above functional residual capacity (FRC) to transpulmonary pressure (PTP) of a lung connected to the breathing apparatus, based on a change in end-expiratory lung volume (ΔEELV) between the first PEEP level and the second PEEP level.

The processing unit is for instance further configured to calculate any one of end-inspiratory transpulmonary pressure (PTPEI), transpulmonary driving pressure (ΔPTPEI), tidal volume (VT) and PEEP from any two of the other of PTPEI, VT and PEEP using the lung mechanics equation.

Alternatively, or in addition, the system can further comprise a display unit operatively connected to the processing unit. The processing unit can be configured to provide on the display unit a graphical visualization of the lung mechanics equation mentioned above.

Alternatively, or in addition, the graphical visualization is a complete lung P/V curve generated using one or more step changes in PEEP level.

Alternatively, or in addition, the system comprises a graphical visualization including information relating breath-by-breath changes in lung volume in response to a change in PEEP level.

Alternatively, or in addition, the control unit is configured to set a desired value of a ventilation parameter in a breathing apparatus, and is configured to calculate a value for PTPEI using the lung mechanics equation calculated as described herein and to select a VT and PEEP based upon the lung mechanics equation.

Alternatively, or in addition, the control unit is configured to adjust at least one second ventilation parameter in the breathing apparatus for a ventilation of a connected patient based on a target input of a first ventilation parameter from a clinical user, and configured to raise a first positive end-expiratory pressure PEEP level to at least a second PEEP level above the first PEEP level and subsequently lowering the second PEEP level to the first PEEP level and adjusting the tidal volume to be equal to the change in end-expiratory lung volume (ΔEELV).

A method 350 is disclosed as an example of setting 370 a desired value of a ventilation parameter in a breathing apparatus. The method comprises calculating 365 a value for PTPEI using the lung mechanics equation being calculated as described herein 360 and selecting a VT and PEEP based upon the lung mechanics equation.

Alternatively, or in addition, a method is disclosed as an example of automatically adjusting at least one second ventilation parameter in a breathing apparatus for a ventilation of a connected patient based on a target input of a first ventilation parameter from a clinical user. The method including for instance raising a first positive end-expiratory pressure PEEP level to at least a second PEEP level above the first PEEP level and subsequently lowering the second PEEP level to the first PEEP level and adjusting the tidal volume to be equal to the change in end-expiratory lung volume (ΔEELV).

Alternatively, or in addition, the method includes calculating a lung mechanics equation relating total lung volume above functional residual capacity (FRC) to transpulmonary pressure (PTP) of a lung connected to the breathing apparatus, based on a change in end-expiratory lung volume (ΔEELV) between the first PEEP level and the second PEEP level, and adjusting at least one of PTPEI, ΔPTP, VT and PEEP based on the lung mechanics equation.

Alternatively, or in addition, the method includes calculating breath-by-breath change in EELV in response to a change in PEEP level from a first PEEP level to a second PEEP level and there from determining whether the lungs exhibit increased, decreased, or constant elastance between the first and second PEEP levels.

Alternatively, or in addition, a software or computer program is provided. It is preferably embodied on a computer-readable medium. The software or computer program includes codes segments or instructions for performing the methods described herein. The software or computer program is preferably executed on a processing unit or control unit, such as that described herein of a breathing apparatus.

Alternatively, or in addition, a graphical user interface for a system described herein is disclosed as an example. The graphical user interface includes a graphical visualization including a combination of values for PTPEI, VT and PEEP wherein at least of the of PTPEI, VT and PEEP values is calculated based on the lung mechanics Equation described herein.

Lung mechanics equation as described herein includes a lung mechanics and chest wall mechanics equation.

Alternatively, or in addition, the system includes a breathing apparatus and a processing unit configured to raise a first positive end-expiratory pressure PEEP level to at least a second PEEP level above the first PEEP level, determine an increase in end expiratory lung volume EELV (ΔEELVup) and subsequently lowering the second PEEP level to the first PEEP level. The processing unit is configured to determine a decrease in EELV (ΔEELVdown), and calculate a change in end-expiratory lung volume (ΔEELVmean) between the first PEEP level and the second PEEP level as (ΔEELVup/ΔEELVdown)/2. The processing unit is further configured to set a tidal volume to be equal to ΔEELVmean, and calculate a lung mechanics and chest wall mechanics equation related to the lung volume between the end-expiratory lung volume at the first PEEP level and the end-expiratory lung volume at the second PEEP level to transpulmonary pressure (PTP) of a lung connected to the breathing apparatus, at the tidal volume equal to ΔEELVmean, as elucidated in examples above.

Alternatively, or in addition, the system includes a clinical decision system. This clinical decision system is for instance a clinical decision support system (CDSS). CDSS are known as devices or applications that provide data analysis to help healthcare providers make clinical decisions. The present disclosure presents specific CDSS previously not known. The clinical decision system includes for instance a graphical user interface of the breathing apparatus, the graphical user interface including a graphical visualization including a combination of values for PTPEI, VT and PEEP, wherein at least of the of PTPEI, VT and PEEP values is calculated based on the lung mechanics and chest wall mechanics equation.

Alternatively, or in addition, the processing unit is further configured to calculate any one of end-inspiratory transpulmonary pressure (PTPEI), transpulmonary driving pressure (ΔPTPEI), tidal volume (VT) and PEEP from any two of the other of PTPEI, VT and PEEP using the lung mechanics equation.

Alternatively, or in addition, the system includes a display unit operatively connected to the processing unit, the processing unit being configured to provide on the display unit a graphical visualization of the lung mechanics equation.

The graphical visualization may be a complete lung P/V curve generated using one or more step changes in PEEP level as elucidated above and shown in the Figures.

The system may alternatively, or in addition, include a graphical visualization including information relating breath-by-breath changes in lung volume in response to a change in PEEP level.

Alternatively, or in addition, the processing unit or control unit is configured to set a desired value of a ventilation parameter in a breathing apparatus, and is configured to calculate a value for PTPEI using the lung mechanics equation described above. The processing unit is alternatively, or in addition, configured to select a VT and PEEP based upon the lung mechanics and chest wall mechanics equation.

Alternatively, or in addition, the processing unit or control unit (interchangeably used expressions herein) is configured to adjust at least one second ventilation parameter in the breathing apparatus for a ventilation of a connected patient based on a target input of a first ventilation parameter from a clinical user. The control unit is for instance configured to raise a first positive end-expiratory pressure PEEP level to at least a second PEEP level above the first PEEP level and subsequently lowering the second PEEP level to the first PEEP level and adjusting the tidal volume to be equal to the change in end-expiratory lung volume (ΔEELV).

Alternatively, or in addition, the a method is provided for adjusting at least one second ventilation parameter in a breathing apparatus for a ventilation of a connected lung, test lung, model lung or artificial lung based on a target input of a first ventilation parameter from a clinical user. The method includes preferably raising a first positive end-expiratory pressure PEEP level to at least a second PEEP level above the first PEEP level, determining an increase in end expiratory lung volume EELV (ΔEELVup) and subsequently lowering the second PEEP level to the first PEEP level. The method also preferably includes determining a decrease in EELV (ΔEELVdown), and calculating a change in end-expiratory lung volume (ΔEELVmean) between the first PEEP level and the second PEEP level as Asecond PEEP level a. The method further can include setting a tidal volume to be equal to ΔEELVmean. The method can include calculating a lung mechanics and chest wall mechanics equation related to the lung volume between the end-expiratory lung volume at the first PEEP level and the end-expiratory lung volume at the second PEEP level to transpulmonary pressure (PTP) of the lung, test lung, model lung or artificial lung connected to the breathing apparatus, at the ΔEELVmean, and adjusting the at least one second ventilation parameter, the at least one second ventilation parameter being at least one of PTPEI, VT and PEEP based on the lung mechanics equation.

The invention claimed is:

1. A system including a breathing apparatus and a processing unit configured to:
   in response to determining it is clinically possible to raise a positive end-expiratory pressure (PEEP) value above a first PEEP level, raise the PEEP level to a second PEEP level above said first PEEP level and subsequently lower said PEEP level from said second PEEP level to said first PEEP level,
   in response to determining it is not clinically possible to increase said PEEP level above the first PEEP level, lower said PEEP to a third PEEP level below said first PEEP level and subsequently raise said PEEP level from said third PEEP level to said first PEEP level,
   adjust a tidal volume (VT) setting of said breathing apparatus to be equal to an absolute value of a change in end-expiratory lung volume (ΔEELV) between said first PEEP level and said second PEEP level or said third PEEP level, and calculate a lung pressure volume (P/V) curve relating total lung volume above functional residual capacity (FRC) to a transpulmonary pressure (PTP) of a lung connected to said breathing apparatus, based on said ΔEELV.

2. The system of claim 1, wherein said processing unit is further configured to calculate any one of end-inspiratory transpulmonary pressure (PTPEI), transpulmonary driving pressure (ΔPTP), VT and PEEP from any two of the other of the PTPEI, the VT and the PEEP.

3. The system of claim 1, further including a display unit operatively connected to said processing unit, said processing unit being configured to provide on said display unit a graphical visualization of said lung pressure volume (P/V) curve.

4. The system of claim 3, wherein said graphical visualization is a complete lung P/V curve generated using one or more step changes in the PEEP level.

5. The system of claim 3, further including a graphical visualization including information relating breath-by-breath changes in lung volume in response to a change in the PEEP level.

6. The system of claim 2, wherein said processing unit is configured to set a desired value of a ventilation parameter in a breathing apparatus, and is configured to calculate a value for PTPEI using said lung mechanics equation calculated by the system of claim 2 and to select the VT and the PEEP based upon said lung P/V curve.

7. The system of claim 1, said processing unit further being configured to adjust at least one second ventilation parameter in said breathing apparatus for a ventilation of a connected patient based on a target input of a first ventilation parameter from a clinical user.

8. The system of claim 1, including a graphical user interface including a graphical visualization including a combination of values for end-inspiratory transpulmonary pressure (PTPEI), VT and PEEP, wherein at least one of said of PTPEI, VT and PEEP values is based on said lung pressure volume (P/V) curve.

9. A system including a breathing apparatus and a processing unit configured to:
raise a first positive end-expiratory pressure (PEEP) level to at least a second PEEP level above said first PEEP level,
determine an increase in end expiratory lung volume (ΔEELVup) and subsequently lowering said second PEEP level back to said first PEEP level,
determine a decrease in EELV (ΔEELVdown),
calculate a mean change in end-expiratory lung volume (ΔEELVmean) between said first PEEP level and said second PEEP level as (ΔEELVup+ΔEELVdown)/2,
set a tidal volume (VT) to be equal to ΔEELVmean, and
calculate lung mechanics and chest wall mechanics equations relating the lung volume between the end-expiratory lung volume at the first PEEP level and the end-expiratory lung volume at the second PEEP level to a transpulmonary pressure (PTP) of a lung connected to said breathing apparatus, at said tidal volume equal to ΔEELVmean.

10. The system of claim 9, including a clinical decisions systems including a graphical user interface of said breathing apparatus, said graphical user interface including a graphical visualization including a combination of values for end-inspiratory transpulmonary pressure (PTPEI), VT and PEEP, wherein at least one of said of PTPEI, VT and PEEP values is calculated based on said lung mechanics and chest wall mechanics equations.

11. The system of claim 9, wherein said processing unit is further configured to calculate any one of end-inspiratory transpulmonary pressure (PTPEI), transpulmonary driving pressure (ΔPTP), VT and PEEP from any two of the other of PTPEI, VT and PEEP using said lung mechanics equation.

12. The system of claim 9, including a display unit operatively connected to said processing unit, said processing unit being configured to provide on said display unit a graphical visualization of said lung mechanics equation.

13. The system of claim 12, wherein said graphical visualization is a complete lung pressure volume (P/V) curve generated using one or more step changes in the PEEP level.

14. The system of claim 12, further including a graphical visualization including information relating breath-by-breath changes in lung volume in response to a change in the PEEP level.

15. The system of claim 11, wherein said processing unit is configured to set a desired value of a ventilation parameter in a breathing apparatus, and is configured to calculate a value for PTPEI using said lung mechanics equation and to select a VT and PEEP based upon said lung mechanics and chest wall mechanics equations.

16. The system of claim 9, said processing unit further being configured to adjust at least one second ventilation parameter in said breathing apparatus for a ventilation of a connected patient based on a target input of a first ventilation parameter from a clinical user, and configured to raise said first PEEP level to at least said second PEEP level above said first PEEP level and subsequently lowering said second PEEP level to said first PEEP level and adjusting the VT to be equal to the change in end-expiratory lung volume (ΔEELV).

17. A system including a breathing apparatus and a processing unit configured to:
lower a positive end-expiratory pressure (PEEP) level from a first PEEP level to a second PEEP level below said first PEEP level in response to determining it is not clinically possible to increase said PEEP level above the first PEEP level,
determine a decrease in end expiratory lung volume (ΔEELVdown) and subsequently increase said PEEP level back to said first PEEP level,
determine an increase in EELV (ΔEELVup),
calculate a mean change in end-expiratory lung volume (ΔEELVmean) between said first PEEP level and said second PEEP level as (ΔEELVup+ΔEELVdown)/2,
set a tidal volume (VT) to be equal to ΔEELVmean, and
calculate a lung mechanics and chest wall mechanics equations relating the lung volume between the end-expiratory lung volume at the first PEEP level and the end-expiratory lung volume at the second PEEP level to transpulmonary pressure (PTP) of a lung connected to said breathing apparatus, at said VT equal to ΔEELVmean.

* * * * *